United States Patent [19]

Steele

[11] Patent Number: 5,073,502
[45] Date of Patent: Dec. 17, 1991

[54] METHOD AND APPARATUS FOR ANALYZING TOTAL ORGANIC HALOGENS

[75] Inventor: John W. Steele, Torrington, Conn.

[73] Assignee: United Technologies Corporation, Hartford, Conn.

[21] Appl. No.: 544,766

[22] Filed: Jun. 27, 1990

[51] Int. Cl.⁵ ............................................. G01N 33/00
[52] U.S. Cl. .................................... 436/125; 436/178;
   436/139; 436/160; 436/161; 436/146; 122/89;
   122/93; 73/23.41
[58] Field of Search .................... 422/89, 93; 436/177,
   436/178, 139, 140, 141, 158, 160, 161, 162, 145,
   146, 128; 73/23.41

[56] References Cited
U.S. PATENT DOCUMENTS

| | | | |
|---|---|---|---|
| 3,860,393 | 1/1975 | Campen, Jr. ...................... | 23/230 R |
| 3,923,460 | 12/1975 | Parrott et al. ...................... | 23/230 R |
| 4,233,030 | 11/1980 | Twitchett et al. .................. | 23/230 R |
| 4,242,097 | 12/1980 | Rich, Jr. et al. .................. | 23/230 R |
| 4,272,246 | 6/1981 | Fritz et al. ......:.................. | 23/230 R |
| 4,288,229 | 9/1981 | Mar ...................................... | 422/79 |
| 4,472,354 | 9/1984 | Panell et al. .......................... | 422/62 |
| 4,672,042 | 1/1987 | Ross, Jr. et al. ..................... | 436/161 |

OTHER PUBLICATIONS

"Amberlite ® Ion Exchange Resins," Technical Notes, Rohm & Haas Co.
Minear & Keith, "Carbon Analyzers: Source of Error," Water Analysis, vol. 3, Academic Press.

Primary Examiner—David L. Lacey
Assistant Examiner—Abanti B. Singla
Attorney, Agent, or Firm—Alan C. Cohen; Pamela J. Mercier

[57] ABSTRACT

The present invention is a single phase analysis process and apparatus which is zero gravity compatible and capable of detecting trace levels of organic halogens. The process utilizes a sorbent bed, oxidation chamber, and an ion chromatograph. Current technology does not allow determination of which organic halogens are present at trace levels. Additionally, the commonly utilized technique for monitoring organic halogens is a two phase analysis which is not zero gravity compatible.

23 Claims, 1 Drawing Sheet

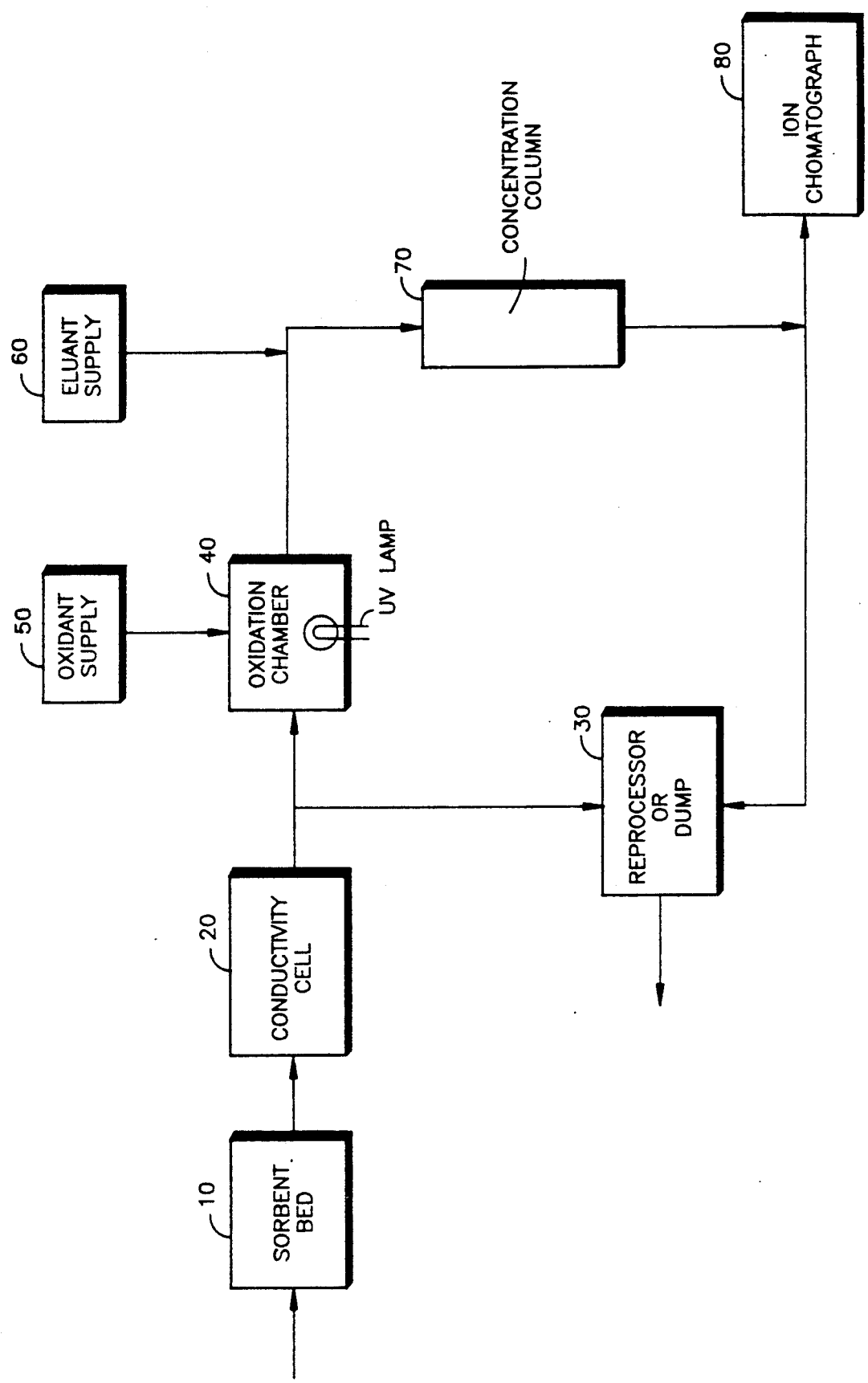

METHOD AND APPARATUS FOR ANALYZING TOTAL ORGANIC HALOGENS

CROSS REFERENCE

This application relates to copending U.S. patent application Ser. No. 07/544,764, for AUTOMATED BIOLUMINESCENCE MICROBIAL MONITOR, filed on June 27, 1990; U.S. patent application Ser. No. 07/544,765, for AN ELUANT STORAGE AND PREPARATION APPARATUS AND METHOD FOR USING THE SAME, filed June 27, 1990; U.S. patent application Ser. No. 07/544,767, for ZERO GRAVITY COMPATIBLE TOTAL ORGANIC AND INORGANIC CARBON ANALYZER, filed June 27, 1990; U.S. patent application Ser. No. 07/544,763, for ZERO GRAVITY PURGE AND TRAP FOR MONITORING VOLATILE ORGANIC COMPOUNDS, filed June 27, 1990; and U.S. patent application Ser. No. 07/544,768, for ZERO GRAVITY COMPATIBLE TOTAL ORGANIC AND INORGANIC CARBON ANALYZER, filed June 27, 1990, all commonly assigned.

DESCRIPTION

1. Technical Field

This invention relates to a halogen analyzer, and especially to an organic halogen analyzer which uses an ion chromatograph.

2. Background Art

Monitoring organic halogen compounds is important in potable water since most are considered potential carcinogens at trace (ppb, parts per billion) levels. Monitoring is especially important when man-made materials are used in water treatment processes or when halogens like chloride or iodine are introduced to the water as biocides because the potential presence of trace organic halogens is high in these instances. Purge and trap techniques are well known in the art for analyzing individual and classes of organic halogens, such as fluorinated, chlorinated, brominated, and iodated hydrocarbons. Conventional analysis techniques for organic halides involve passing water through an activated charcoal bed to trap organic and inorganic halogens. The inorganic halogens are liberated from the trap with a nitric acid solution at a pH of about 2. The trapped organic halogens are pyrolyzed from the trap at about 900° C. while passing an oxygen rich carrier stream through the charcoal bed. The organic halogens are converted to acid halides, bubbled into a microcoulometer cell, and titrated with silver chloride to quantitate with current measurements. This technique fails to identify the type of organic halogen present; it does not differentiate chlorine from fluorine from iodine. This technique is also labor intensive, requires a gas to liquid phase change which creates problems in a zero gravity environment, and is only capable of detecting a small percentage of the organic halogens present.

Since each organic halogen has varying health considerations, specific halide type identification is desirable. Therefore, what is needed in the art is a total organic halogen analysis process which is zero gravity compatible, can run in a single phase, can be automated, and in which the specific halogen can be identified.

DISCLOSURE OF INVENTION

The present invention is an apparatus for monitoring total organic halogen concentration in a liquid and a process for using the same. The apparatus is comprised of a means for removing inorganic halogens from a liquid sample, an oxidation chamber for converting the organic halogens to ionic halides, and an ion chromatograph for analyzing the ionic halides. Inorganic halogens are removed from a liquid sample prior to the sample entering the oxidation chamber where the organic halogens are converted to ionic halides and carbonate (hereafter referred to as ionic halides). The ionic halides are then analyzed in the ion chromatograph.

The foregoing and other features and advantages of the present invention will become more apparent from the following description and accompanying drawing.

BRIEF DESCRIPTION OF DRAWINGS

The Figure is a schematic of one possible embodiment of the total organic halogen analyzer of the present invention.

BEST MODE FOR CARRYING OUT THE INVENTION

The present invention is a total organic halogen analyzer and method for using the same. The monitor performs a single phase analysis on a liquid, detecting total organic halide concentration and the specific halogens present. The monitor is comprised of: a means for removing inorganic halogen from a liquid, an oxidation chamber, and an ion chromatograph. Inorganic halogen is removed from the liquid sample. The inorganic halogen free sample then enters the oxidation chamber where the organic halogens (OX) are converted to carbonate ($CO_3^=$) and halide ions ($X^-$):

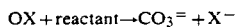

$$OX + reactant \rightarrow CO_3^= + X^-$$

The ionic halides then flow through the ion chromatograph where they are analyzed.

Organic halogens can be monitored in any liquid which does not adversely affect the analyzer. A test sample is drawn from the liquid to be monitored and the inorganic halogen in the liquid sample is removed. Any means for removing inorganic halogens from a liquid sample can be used, such as intimately contacting the liquid sample with a sorbent bed. The sorbent bed can be any sorbent bed conventionally known in the art which is capable of separating inorganic halogens from organic halogens in a liquid by trapping the inorganic halogens. Typical sorbent beds include mixed resin beds of which any strong base/strong acid cation/anion exchange resin mix can be utilized, such as the sulfonated polystyrene and tetramethyl ammonium styrene mixed bed. Note, many sorbent beds require preconditioning prior to use because the initial sorbent bed effluent is conductive and can potentially invalidate the analysis. Preconditioning consists of flowing a liquid, such as deionized water, through the sorbent bed and using a conductivity cell or other means of detecting the conductivity of a liquid conventionally known in the art. Typically, a reading of about 18 megaohm or greater is sufficient for the sorbent bed to be deemed conditioned.

Once the inorganic halogen free sample exits the preconditioned sorbent bed it enters an oxidation chamber where the organic halogens are converted to halide ions and carbonate The process requires introducing a means for oxidizing to the oxidation chamber. Any means for oxidizing conventionally known in the art which is capable of oxidizing the organic halogen compounds to conductive ionic halides and carbonate and can operate in temperatures up to at least about 115° F., such as oxidants and an ultraviolet (UV) radiation produced with UV lamps or bulbs, and combinations thereof, can be used. Possible oxidants include potassium persulfate and sodium dichromate. Note, higher temperatures can adversely effect the ion chromatograph analysis.

After the organic halogen compounds are converted to ionic halides, they are analyzed in an ion chromatograph, or any other analysis device known in the art for detecting ionic halides and carbonate.

Concentration of the sample may be necessary due to the ion chromatograph's sensitivity restrictions. This can be accomplished by using any means conventionally known in the art from concentrating ionic halides, such as a concentration column or anion concentration column. If a concentration column is used, it must be capable of trapping, adsorbing or absorbing, ionic halides upon intimate contact with the oxidized sample. Examples of such columns include strong acid/strong base mixed ion exchange beds such as sulfonated polystyrene and tetra methyl ammonium styrene. The amount of liquid to pass through the column is determined empirically according to the desired maximum amount of organic halogens allowable in the liquid being analyzed and the sensitivity of the ion chromatograph. For example, if 1 ppb is the maximum allowable amount of organic halogen in the potable water, then 50 ml of the water would be intimately contacted with the concentration column if the sensitivity of the ion chromatograph is 1 ppm and the sample loop is 50 microliters.

If a concentration column is used to concentrate the ionic halides, they can be liberated by flowing an eluant through the concentration column. The eluant liberates the ionic halides and carries them to the ion chromatograph for analysis. Any eluant which elutes the ionic halides bound to the concentration column and which does not adversely effect the ion chromatograph analysis, can be used, such as dilute sodium carbonate/sodium bicarbonate and sodium hydroxide/sodium carbonate, among others. Yet, if a concentration column is not used to concentrate the ionic halides, any means conventionally know in the art for introducing the concentrated ionic halides to the ion chromatograph can be used.

Having been converted and concentrated, the ionic halides are analyzed in the ion chromatograph. The ion chromatograph establishes the types and amounts of halides present in the sample via an adsorption/desorption process. Since the adsorption/desorption cycle time, "retention time", varies according the the species, certain species are detected in the detector at different times. This enables the various species to be distinguished from one another. Note, any monitoring device capable of detecting the amount and type of halogens present, such as ion selective electrodes and a simple conductivity cell coupled to known ionic halide retention times as is well know in the art, can be utilized. Also, preconditioning of the ion chromatograph in order to flush out any contaminants and to zero the instrument prior to an analysis is recommended for more accurate results.

Referring to the Figure, which is meant to be exemplary not limiting, the analyzer of the present invention has a sorbent bed (10) which is conditioned by flowing liquid through the sorbent bed (10) through the conductivity cell (20) to a reprocessing reservoir or dump (30).

During sorbent bed (10) conditioning, the ion chromatograph (80) is conditioned and flushed with an eluant. Once the sorbent bed (10) has been conditioned, a liquid sample is intimately contacted with the sorbent bed (10) to remove any inorganic halogens. As the inorganic halogen free sample enters the oxidation chamber (40), oxidant is added to the oxidation chamber (40) from the means for supplying oxidant (50). The inorganic halogen free sample is oxidized with an oxidant and an ultraviolet (UV) lamp (45), which produces UV radiation, in the oxidation chamber (40). Upon conversion of the organic halogens to ionic halides, the oxidized sample enters the concentration column (70) where the ionic halides are removed, concentrating the ionic halides. After sufficient oxidized sample has passed through the concentration column (70), the inorganic halogen free sample flow is halted and eluant is passed through the concentration column (70) from the means for supplying eluant (60). The eluant liberates the concentrated ionic halides and carries them to the ion chromatograph (80) for analysis. As is commonly known in the art, within the conventional ion chromatograph (80) the halides are separated by an adsorption/desorption process. Since various halides' retention times differ, the halides pass through the ion chromatograph (80) at different rates, allowing the type and concentration to be determined.

EXAMPLE

The following can be used to test water for the presence of 1 ppb of organic halogen compounds in water.

1. The sorbent bed, 16 to 50 mesh sulfonated polystyrene and tetramethyl ammonium styrene mixed resin bed is preconditioned by passing 100 milliliters of deionized water through the bed at 5.0 ml/min, while the ion chromatograph (80) is zeroed and preconditioned with dilute sodium carbonate/sodium bicarbonate (3 mM (millimolar) sodium carbonate and 2.4 mM sodium bicarbonate), eluant.
2. 50 (ml) of water sample is passed through the sorbent bed (10) at 3.0 ml/min to remove the inorganic halogens.
3. The inorganic halogen free water sample proceeds into the oxidation chamber (40) where the organic halogen compounds are oxidized to ionic halides and carbonate with potassium persulfate which enters the oxidation chamber (40) at 1.0 ml/min and UV radiation from a UV lamp (45).
5. The oxidized water sample then passes through the concentration column (30) where the ionic halides are trapped and the spent water sample proceeds to the reprocessing reservoir (30).
6. Once 50 ml of oxidized water sample has passed through the concentration chamber (70), eluant is passed through the concentration column (70) at 3.0 ml/min. liberating the ionic halides and carrying them to the ion chromatograph (80) for analysis.

Unlike the prior art, this process is a single phase analysis for organic halogen compounds and can be operated in a zero gravity environment; is zero gravity compatible. Additionally, the present invention allows for the detection and identification of total organic halogens, even at trace levels. This enables, for example, a more accurate determination of the health effects of the liquid being tested.

Although this invention has been shown and described with respect to detailed embodiments thereof, it will be understood by those skilled in the art that various changes in form and detail thereof may be made without departing from the spirit and scope of the claimed invention.

I claim:

1. A method for detecting the presence of organic halogens in a liquid, which comprises:
   a. removing any inorganic halogen from a liquid sample containing any organic halogens;
   b. converting the organic halogens in the inorganic halogen free liquid sample to ionic halides;
   c. analyzing the ionic halides in an ion chromatograph so as to provide an indication of the presence of organic halogens.

2. A method as in claim 1 wherein the liquid sample is water.

3. A method as in claim 1 wherein the inorganic halogens are removed from the liquid sample by intimately contacting the liquid sample with a sorbent bed.

4. A method as in claim 3 wherein the sorbent bed is selected from the group consisting of sulfonated polystyrene and tetra methyl ammonium styrene, strong base/strong acid mixed bed ion exchange resin, and mixtures of the same.

5. An apparatus for detecting the presence of organic halogens in a liquid, which comprises:
   a. a means for removing inorganic halogens from a liquid sample;
   b. an oxidation chamber constructed so as to receive the inorganic halogen free liquid sample said oxidation chamber in flow communication with said means for removing inorganic halogens and said oxidation chamber further constructed so as to oxidize organic halogens in the inorganic halogen free liquid sample to ionic halides;
   c. an ion chromatograph constructed so as to analyze the ionic halides so as to provide an indication of the presence of organic halogens.

6. An apparatus as in claim 5 wherein the means for removing inorganic halogens is a sorbent bed.

7. An apparatus as in claim 6 wherein the sorbent bed is selected from the group consisting of sulfonated polystyrene and tetramethyl ammonium styrene, and strong base/strong acid mixed bed ion exchange resins.

8. An apparatus for detecting the presence of organic halogens in liquid, which comprises:
   a. a means for removing inorganic halogens from a liquid sample;
   b. an oxidation chamber constructed so as to receive the inorganic halogen free liquid sample said oxidation chamber in flow communication with said means for removing inorganic halogens and said oxidation chamber further constructed so as to oxidize organic halogens in the inorganic halogen free liquid sample to ionic halides;
   c. a means for concentrating the ionic halides said means for concentrating ionic halides in flow communication with said oxidation chamber;
   d. a means for introducing said concentrated ionic halides to an ion chromatograph so as to analyze said concentrated ionic halides said means for introducing said concentrated ionic halides in flow communication with said means for concentrating ionic halides, said ion chromatograph constructed so as to provide an indication of the presence of organic halogens.

9. An apparatus as in claim 8 wherein the means for removing inorganic halogens is a sorbent bed.

10. An apparatus as in claim 9 wherein the sorbent bed is selected from the group consisting of sulfonated polystyrene, tetramethyl ammonium styrene, strong base/strong acid mixed bed ion exchange resin, and mixtures of the same.

11. An apparatus as in claim 8 wherein, said oxidizing chamber comprises means for oxidizing the organic halogens, said oxidizing means selected from the group consisting of an oxidant, ultraviolet lamps and bulbs, and combinations thereof.

12. An apparatus as in claim 8 wherein the means for concentrating ionic halides is a concentration column.

13. An apparatus as in claim 8 wherein the means for introducing concentrated ionic halides to the ion chromatograph is an eluant means.

14. A method for detecting the source of organic halogens in a liquid, which comprises:
   a. removing any inorganic halogens from a liquid sample containing organic halogens;
   b. converting the organic halogens in the inorganic halogen free liquid sample to ionic halides;
   c. concentrating the ionic halides;
   d. analyzing the ionic halides in an ion chromatograph so as to provide an indication of the presence of organic halogens.

15. A method as in claim 14 wherein the liquid sample is water.

16. A method as in claim 14 wherein the inorganic halogens are removed from the liquid sample by a sorbent bed.

17. A method as in claim 16 wherein the sorbent bed is selected from the group consisting of sulfonated polystyrene, tetramethyl ammonium styrene, strong base/strong acid mixed bed ion exchange resin, and mixtures of the same.

18. A method as in claim 14 wherein the organic halogens are converted to ionic halides using a means selected from the group consisting of an oxidant, ultraviolet lamps and bulbs, and combinations thereof.

19. A method as in claim 18 wherein the oxidant is selected from the group consisting of potassium persulfate and sodium dichromate.

20. A method as in claim 14 wherein the ionic halides are concentrated in a concentration column which traps the ionic halides.

21. A method as in claim 20 wherein the ionic halides liberated from the concentration column using an eluant.

22. A method as in claim 21 wherein the eluant is selected from the group consisting of dilute sodium carbonate/sodium bicarbonate and sodium hydroxide/sodium carbonate.

23. A zero gravity compatible apparatus for detecting the presence of organic halogens in a liquid, which comprises:
   a. a sorbent bed constructed so as to remove inorganic halogen from a liquid sample;
   b. an oxidation chamber constructed so as to receive the inorganic halogen free liquid sample, said oxidation chamber in flow communication with said sorbent bed, and said oxidation chamber further constructed so as to oxidize organic halogens in the inorganic halogen free liquid sample to ionic halides; and
   c. an ion chromatograph constructed so as to analyze the ionic halides so as to provide an indication of the presence of organic halogens.

* * * * *

UNITED STATES PATENT AND TRADEMARK OFFICE
CERTIFICATE OF CORRECTION

PATENT NO. : 5,073,502
DATED : December 17, 1991
INVENTOR(S) : John W. Steele

It is certified that error appears in the above-identified patent and that said Letters Patent is hereby corrected as shown below:

IN THE CLAIMS

Claim 14, Column 6, Line 18, "source" should be --presence--

Signed and Sealed this

First Day of June, 1993

Attest:

MICHAEL K. KIRK

Attesting Officer  Acting Commissioner of Patents and Trademarks